US008404253B2

(12) United States Patent
Oliveira et al.

(10) Patent No.: US 8,404,253 B2
(45) Date of Patent: Mar. 26, 2013

(54) MODIFIED LIVE (JMSO STRAIN) *HAEMOPHILUS PARASUIS* VACCINE

(75) Inventors: Simone R. Oliveira, New Brighton, MN (US); Randy R. Simonson, Worthington, MN (US); Jonathan D. Mahlberg, Worthington, MN (US); Mark D. Titus, Jackson, MN (US); Tracy A. Oleson, Lake Park, WI (US)

(73) Assignee: Newport Laboratories, Inc.

( * ) Notice: Subject to any disclaimer, the term of this patent is extended or adjusted under 35 U.S.C. 154(b) by 1825 days.

(21) Appl. No.: 11/648,390

(22) Filed: Dec. 28, 2006

(65) Prior Publication Data

US 2010/0255035 A1 Oct. 7, 2010

(51) Int. Cl.

| | |
|---|---|
| ***A61K 39/102*** | (2006.01) |
| ***A61K 48/00*** | (2006.01) |
| ***A01N 63/00*** | (2006.01) |
| ***A01N 65/00*** | (2009.01) |

(52) U.S. Cl. .................. 424/256.1; 424/93.1; 424/93.2; 424/93.4

(58) Field of Classification Search ........................ None
See application file for complete search history.

(56) References Cited

U.S. PATENT DOCUMENTS

| | | | | |
|---|---|---|---|---|
| 6,783,764 B1 * | 8/2004 | Segers et al. | ............... | 424/236.1 |
| 7,879,337 B2 * | 2/2011 | Yoo et al. | ................... | 424/204.1 |
| 8,021,670 B2 * | 9/2011 | Drexler et al. | ............ | 424/201.1 |
| 2002/0068068 A1 * | 6/2002 | Mahan et al. | ............. | 424/200.1 |
| 2007/0082009 A1 | 4/2007 | Lawrence et al. | | |
| 2010/0255035 A1 * | 10/2010 | Oliveira et al. | ........... | 424/256.1 |
| 2010/0285070 A1 * | 11/2010 | Bensaid et al. | ........... | 424/256.1 |

FOREIGN PATENT DOCUMENTS

| | | | |
|---|---|---|---|
| RU | 2103355 C1 | | 1/1998 |
| WO | WO 2004/064776 A2 | | 8/2004 |
| WO | WO 2007/039070 A2 | * | 4/2007 |
| WO | WO 2008/085406 | * | 7/2008 |
| WO | WO 2011/056954 A2 | * | 5/2011 |

OTHER PUBLICATIONS

Takahashi et al, J. Vet. Med. Sci., 2001, 63/5:487-491.*
Bak et al, Vet. Rec., Oct. 26, 2002, 151/17:502-505.*
Turni, In: Controlled exposure as a management tool for Glaesser's Disease, 2010, abstract only.*
Blanco et al, Vet. Microbiology, 2004, 103:21-27.*
Maclnnes et al, Can. J. Vet. Res, 1999, 63:83-89.*
Rapp-Gabrielson et al, Vet. Medicine, 1997, 92/1:83-90.*
Bigas et al, Vet. Microbiol, 2005, 105:223-228.*
Oliveira et al, American J. Vet. Research, Apr. 2003, 64/4:435-442 abstract only.*
Hooke, A. M. et al.; "Live attenuated bacterial vaccines: new approaches for safety and efficacy"; Lancet, Jun. 29, 1985, vol. 1, No. 8444; pp. 1472-1474, XP002484737; ISSN: 0140-6736.
Linde, K.; "Use of attenuated mutants of *Pasteurella multocida* strain, pathogenic to calves, in experimental mouse model studies"; Archiv für Experimentelle Veterinärmedizin; vol. 32, No. 6, 1978; pp. 943-949; XP009101801 ISSN: 0003-9055.
Database EMBL *Haemophilus parasuis* Apr. 16, 2005, "*Haemophilus parasuis* ribosomal protein S12 (res12) gene, complete cds" XP002484740 retrieved from EBI Database accession No. AY236072 abstract.
Bigas et al.; "Development of a genetic manipulation system for *Haemophilus parasuis*"; Veterinary Microbiology, Amsterdam, NL, vol. 105, No. 3-4, Feb. 25, 2005, pp. 223-228.
Stuy, J.H. et al; "Cloning, characterization, and DNA base sequence of the high-level streptomycin resistance gene strA1 of *Haemophilus influenzae* Rd."; Journal of Bacteriology; Sep. 1992, vol. 174, No. 17, pp. 5604-5608.
R. Nielsen; "Pathogenicity and immunity studies of *Haemophilus parasuis* serotypes"; Acta Veterinaria Scandinavica; vol. 34, No. 2, 1998, pp. 193-198.
K. Linde et al.; "Stable Listeria monocytogenes live vaccine candidate strains with graded attenuation on the mouse model"; Vaccine, Butterworth Scientific; Guildford, GB; vol. 9, No. 2; Feb. 1, 1991; pp. 101-105.
Anna Bigas et al.; "Colonization capacity and serum bactericidal activity of *Haemophilus parasuis* thy mutants"; International Microbiology; vol. 9, No. 4, Dec. 2006, pp. 297-301.
Simone Oliveira et al.; "*Haemophilus parasuis*: New trends on diagnosis, epidemiology and control" Veterinary Microbiology; vol. 99, No. 1, Mar. 26, 2004, pp. 1-12.

* cited by examiner

*Primary Examiner* — Nita M Minnifield
(74) *Attorney, Agent, or Firm* — Judy Jarecki-Black; Chad Kitchen; Merial Limited

(57) ABSTRACT

The present invention is a culture of cells of *Haemophilus parasuis* exhibiting attenuated pathogenicity and capable of triggering a protective immune response when administered to pigs as a live vaccine. The present invention is also a method of preparing the cell culture, a method of preparing a vaccine from the cell culture, and a live vaccine based on the cell culture. The cell culture was modified from a pathogenic parent strain by MNNG mutagenesis and was selected by complete dependence on streptomycin for growth.

27 Claims, No Drawings

SEQUENCE LISTING

<160> NUMBER OF SEQ ID NOS: 6

<210> SEQ ID NO 1
<211> LENGTH: 375
<212> TYPE: DNA
<213> ORGANISM: Haemophilus parasuis

<400> SEQUENCE: 1

```
atggcaacta tcaaccagct agtacgcaaa ccgcgtgtga aaaaggttgt aaaaagcaac      60

gttcctgcat tagaggcttg cccgcagaaa cgtggtgtgt gtactcgtgt atacactaca     120

actcctaaaa aaccaaactc agcgttacgt aaagtatgtc gtatccgctt aacaaacggt     180

tttgaagtaa cttcttatat cggtggtgaa ggtcacaacc ttcaagagca cagtgttgtg     240

ttaatccgtg gtggtcgtgt taaagactta ccgggtgtgc gttatcacac tgtacgtggt     300

gcacttgact gtgcaggcgt taaagaccgt aaacaaggtc gttctaaata cggcgttaaa     360

cgtcctaagt cttaa                                                      375
```

<210> SEQ ID NO 2
<211> LENGTH: 375
<212> TYPE: DNA
<213> ORGANISM: Haemophilus parasuis

<400> SEQUENCE: 2

```
atggcaacta tcaaccagct agtacgcaaa ccgcgtgtga aaaaggttgt aaaaagcaac      60

gttcctgaat tagaggcttg cccgcagaaa cgtggtgtgt gtactcgtgt atacactaca     120

actcctaaaa aaccaaactc agcgttacgt aaagtatgtc gtatccgctt aacaaacggt     180

tttgaagtaa cttcttatat cggtggtgaa ggtcacaacc ttcaagagca cagtgttgtg     240

ttaatccgtg gtggtcgtgt taaagactta ctgggtgtgc gttatcacac tgtacgtggt     300

gcacttgact gtgcaggcgt taaagaccgt aaacaaggtc gttctaaata cggcgttaaa     360

cgtcctaagt cttaa                                                      375
```

<210> SEQ ID NO 3
<211> LENGTH: 124
<212> TYPE: PRT
<213> ORGANISM: H.parasuis

<400> SEQUENCE: 3

```
Met Ala Thr Ile Asn Gln Leu Val Arg Lys Pro Arg Val Lys Lys Val
1               5                   10                  15

Val Lys Ser Asn Val Pro Ala Leu Glu Ala Cys Pro Gln Lys Arg Gly
            20                  25                  30

Val Cys Thr Arg Val Tyr Thr Thr Thr Pro Lys Lys Pro Asn Ser Ala
        35                  40                  45

Leu Arg Lys Val Cys Arg Ile Arg Leu Thr Asn Gly Phe Glu Val Thr
    50                  55                  60

Ser Tyr Ile Gly Gly Glu Gly His Asn Leu Gln Glu His Ser Val Val
65                  70                  75                  80

Leu Ile Arg Gly Gly Arg Val Lys Asp Leu Pro Gly Val Arg Tyr His
                85                  90                  95

Thr Val Arg Gly Ala Leu Asp Cys Ala Gly Val Lys Asp Arg Lys Gln
            100                 105                 110

Gly Arg Ser Lys Tyr Gly Val Lys Arg Pro Lys Ser
        115                 120
```

-continued

```
<210> SEQ ID NO 4
<211> LENGTH: 124
<212> TYPE: PRT
<213> ORGANISM: H.parasuis

<400> SEQUENCE: 4

Met Ala Thr Ile Asn Gln Leu Val Arg Lys Pro Arg Val Lys Lys Val
1               5                   10                  15

Val Lys Ser Asn Val Pro Glu Leu Glu Ala Cys Pro Gln Lys Arg Gly
            20                  25                  30

Val Cys Thr Arg Val Tyr Thr Thr Thr Pro Lys Lys Pro Asn Ser Ala
        35                  40                  45

Leu Arg Lys Val Cys Arg Ile Arg Leu Thr Asn Gly Phe Glu Val Thr
    50                  55                  60

Ser Tyr Ile Gly Gly Glu Gly His Asn Leu Gln Glu His Ser Val Val
65                  70                  75                  80

Leu Ile Arg Gly Gly Arg Val Lys Asp Leu Leu Gly Val Arg Tyr His
                85                  90                  95

Thr Val Arg Gly Ala Leu Asp Cys Ala Gly Val Lys Asp Arg Lys Gln
            100                 105                 110

Gly Arg Ser Lys Tyr Gly Val Lys Arg Pro Lys Ser
        115                 120


<210> SEQ ID NO 5
<211> LENGTH: 18
<212> TYPE: DNA
<213> ORGANISM: Haemophilus parasuis
<220> FEATURE:
<221> NAME/KEY: misc_feature
<223> OTHER INFORMATION: forward primer

<400> SEQUENCE: 5

tacgcaaacc gcgtgtga                                                   18


<210> SEQ ID NO 6
<211> LENGTH: 20
<212> TYPE: DNA
<213> ORGANISM: Haemophilus parasuis
<220> FEATURE:
<221> NAME/KEY: misc_feature
<223> OTHER INFORMATION: reverse primer

<400> SEQUENCE: 6

tgcgtgcttc aacactacga                                                 20
```

MODIFIED LIVE (JMSO STRAIN) *HAEMOPHILUS PARASUIS* VACCINE

BACKGROUND OF THE INVENTION

*Haemophilus parasuis* is an early colonizer of the upper respiratory tract of pigs. Non-virulent strains of this organism can be normally isolated from the nasal cavity, tonsil, and trachea of healthy pigs. Virulent strains of *H. parasuis* can also invade the host and cause systemic lesions characterized by fibrinous polyserositis, arthritis and meningitis.

Recent studies have demonstrated that non-virulent strains are more prevalent in the upper respiratory tract than virulent strains. However, even though the majority of pigs are colonized by non-virulent *H. parasuis* strains, they are not protected against systemic infection by virulent strains. It is widely recognized in the vaccine field that live vaccines may sometimes provide a higher degree and broader range of protective immunity than killed vaccines.

Controlled exposure to a low dose of live, virulent *H. parasuis* may reduce nursery mortality more efficiently than vaccination using commercial or autogenous killed products. However, exposure to live virulent bacteria poses significant risk of the very disease one is trying to protect against. Attenuation of the virulence of the vaccine strain in a way that is stable and also retains the immunogenicity of the live organism is therefore highly desirable to vaccine development.

Although neither the mechanisms involved in the protective immunity following controlled exposure, nor the identity of antigens which provide protective immunity, are clear at this time, it is known that protective immunity can be induced by such exposure. Moreover, pigs with controlled exposure to live *H. parasuis* are protected against homologous challenge through intratracheal and intraperitoneal routes, suggesting that exposed pigs develop local immune response (upper respiratory tract) as well as a systemic response. Live organisms undergo limited replication in the host at sites of infection and may thereby elicit additional arms of the immune response (e.g., local immunity) and/or augment the level of the response.

*Haemophilus parasuis* killed products (commercial or autogenous) are known to generate poor cross-protection against different serovars. This may be due to incomplete expression of potential virulence factors when this organism is grown in vitro. Live organisms are more likely to express a wide variety of proteins and factors required for growth in vivo. Iron-regulated outer membrane proteins (IROMPS) are an example of potential virulence factors that may be expressed in vivo, but are rarely expressed in vitro. A modified live vaccine would be capable of expressing virulence factors when administered to a host. Most likely this product would induce a more involved immune response creating the potential for a safe more efficacious vaccine.

The pork industry is in need of a safe and efficacious product capable of aiding the prevention of disease due to multiple serotypes of *Haemophilus parasuis*.

SUMMARY OF THE INVENTION

In a first aspect, the present invention provides cultures of cells of a strain derived from a pathogenic parent strain of a species of *H. parasuis*, which cells exhibit attenuated pathogenicity compared to the parent strain but which are capable of triggering an immune response that protects pigs against infection when administered as a live vaccine.

In a second aspect, the present invention provides vaccines to provide cross-serovar protection for pigs against infection by *H. parasuis*, comprising an immunologically effective amount of live cells of a strain derived from a pathogenic parent strain of the organism, which cells exhibit attenuated pathogenicity compared to those of the parent strain but which are capable of triggering an immune response that protects the animals against infection when administered as a live vaccine, and a veterinarily acceptable carrier. Vaccines of the invention may further comprise one or more other components including, for example, an adjuvant.

In a third aspect, the present invention provides methods for preparing cultures of attenuated cells from a pathogenic strain of *H. parasuis* for use in a vaccine that protects pigs against infection, comprising modifying cells from a pathogenic parent strain of the organism; selecting and clonally propagating one or more modified cells that exhibit attenuated pathogenicity compared to cells of the parent strain; and selecting and clonally propagating one or more attenuated cells which are capable of triggering an immune response that protects the animal against infection when administered in a live vaccine.

In a fourth aspect, the present invention provides methods for preparing a vaccine that protects pigs against infection by *H. parasuis*, comprising modifying cells of a parent strain of the organism; selecting and clonally propagating those modified cells that exhibit attenuated pathogenicity compared to cells of the parent strain; and selecting and clonally propagating one or more attenuated cells which are capable of triggering an immune response that protects the animal against infection when administered as a live vaccine.

DETAILED DESCRIPTION OF THE PREFERRED EMBODIMENT

Applicants have discovered that cells of a pathogenic strain of *Haemophilus parasuis* may be attenuated, and that the resulting attenuated cells are capable of triggering an immune response that protects pigs against *Haemophilus parasuis* infection when administered as a live vaccine.

The present invention further provides a method for preparing cultures of attenuated cells of a pathogenic strain of *Haemophilus parasuis* for use in a vaccine that protects a pig against *Haemophilus parasuis* infection, comprising modifying cells from a pathogenic parent strain of *Haemophilus parasuis* using the mutagen MNNG, selecting and clonally propagating one or more modified cells that dependent on streptomycin for growth and which exhibit attenuated pathogenicity compared to cells of the parent strain; and selecting and clonally propagating one or more attenuated cells which are capable of triggering an immune response that protects the pig against *Haemophilus parasuis* infection when administered in a live vaccine.

The term "attenuated" as used herein describes a cell, culture, or strain of *Haemophilus parasuis* exhibiting a detectable reduction in infectivity or virulence in vivo as compared to that of the parent strain of *Haemophilus parasuis* from which the attenuated cell, culture, or strain is derived. Reduction in virulence encompasses any detectable decrease in any attribute of virulence, including infectivity in vivo, or any decrease in the severity or rate of progression of any clinical symptom or condition associated with infection.

The present invention further encompasses preparation and use in a vaccine of cells of a strain of *Haemophilus parasuis* derived from a pathogenic parent strain of *Haemophilus parasuis* and which exhibit attenuated pathogenicity compared to cells of the parent strain and which are capable of triggering an immune response that protects pigs against *Haemophilus parasuis* infection.

The live attenuated cells of the invention are capable of triggering an immune response that protects pigs against *Haemophilus parasuis* infection after one or more administrations as a live vaccine. A "protective immune response" is defined as any immunological response, either antibody or cell mediated immunity, or both, occurring in the pig that either prevents or detectably reduces subsequent infection, or eliminates or detectably reduces the severity, or detectably slows the rate of progression, of one or more clinical symptoms or conditions associated with *Haemophilus parasuis* infection. The term "immunologically effective amount" refers to that amount or dose of vaccine or antigen that triggers a protective immune response when administered to the pig.

Example 1

Identification of the Parent Strain

The parental strain has been identified as serovar 5, *Haemophilus parasuis*; Newport Laboratories reference no. 3-0930-1.

The isolate was received by Newport Laboratories from Iowa State University Veterinary Diagnostic Laboratory as an agar slant labeled Hps 1888 on May 2, 2003. The isolate was identified as *H. parasuis* based on biochemical reactions (non-hemolytic, v-factor dependent, urea, and arabinose negative). The isolate was identified as a serovar 5, *H. parasuis* by the Faculty of the Veterinary Medicine Department of the University of Montreal.

Example 2

Development of the Vaccine Strain (a) Procedures used to attenuate the parental strain: Attenuation of the parent strain was accomplished by chemical mutagenesis with N-methyl-N'-nitroso-N-nitrosoguanidine (MNNG) and selection for growth dependence on media containing 400 micrograms per mL streptomycin sulfate.

The protocol for MNNG mutagenesis was adapted from Lopes et al., 2001. The parent strain was initially checked for purity by inoculating the culture on 5% sheep blood agar containing a nurse *Staphylococcus* sp. streak and incubating for 24 h at 37° C.+−2° C. in a candle jar.

The culture was pure, based on the absence of extraneous growth outside the *Staphylococcus* sp. streak and growth of the *H. parasuis* satellite colonies in the area adjacent to and just outside the streak. After purity was confirmed, the parent *H. parasuis* strain was swabbed on chocolate agar plates. Plates were incubated as indicated above. The resulting bacterial cells were harvested by adding 1 mL of PBS to the chocolate agar plate and scraping colonies using a sterile, modified Pasteur pipet (heated and bent to the shape of a hockey stick).

Bacterial cells were pooled to one side of the plate, and an automated Pipet-Aid and a 5 mL pipet were used to collect the cell suspension. The cell suspension was then diluted in pre-warmed PPLO media (BD) containing MNNG (Sigma-Aldrich Cp., St. Louis, Mo., 30 micrograms/mL). The mixture of cells and MNNG was then incubated at 37° C.+/−2° C. for 30 minutes without agitation. Following incubation, bacteria were collected by centrifugation and washed with cold phosphate-buffered saline (PBS), pH 7.4, to eliminate residual mutagen. The washed cells were resuspended in pre-warmed PPLO media and incubated at 37° C.+/−2° C. for 40 min.

The MNNG-exposed bacteria were plated onto PPLO agar plates containing 400 mcg/mL streptomycin sulphate and onto PPLO without streptomycin sulphate and both sets of plates were incubated at 37° C.+/−2° C. for 24 hours in a candle jar. PPLO agar plates without streptomycin were used to ensure the MMNG treatment did not inactivate all bacterial cells.

Following incubation, the plates without streptomycin showed bacterial growth, confirming that the MNNG treatment did not inactivate all bacterial cells. A single colony was observed and harvested from a single PPLO plate containing streptomycin sulphate. This colony was passed to a PPLO agar plate and PPLO broth, both supplemented with 400 mcg/mL streptomycin sulphate (permissive media), and to PPLO broth and agar plate containing no streptomycin sulphate (non-permissive). Cultures were incubated as above. Growth on permissive medium and lack of growth on non-permissive medium was seen. This was the basis for selection of the modified live, streptomycin-dependent, Hps vaccine strain. The attenuated *H. parasuis* strain and proposed Master Seed has been identified, "Haemophilus parasuis streptomycin dependent Master Seed 101304".

The selected Master Seed has proven to be avirulent for the natural host of *H. parasuis* (pigs) in preliminary research. A backpassage study of 4 passes with two pigs per pass was completed.

Two pigs were inoculated intraperitoneally with 3 cc of $10^9$ cells of the streptomycin dependent strain. Two days following inoculation, pigs were euthanized and intraperitoneal fluids were collected and passed to 2 additional pigs. This was done for a total of 4 passes. Animals were observed for clinical signs following inoculation and for clinical lesions following euthanasia. Tissues and swabs were taken from euthanized pigs and isolation of the vaccine strain and potential revertant strain was attempted. Approximately 1 mL of the subcultured peritoneal fluid was tested at Newport Laboratories for Hps isolation (as above) and by Hps detection PCR.

Following the administration of the vaccine strain in the backpassage and safety studies, no clinical signs associated with disease caused by Hps were noticed in any pigs. All isolation attempts for the vaccine strain and the streptomycin-independent revertant strain were negative. Hps detection PCR from peritoneal fluid from the preliminary backpassage study was negative.

(b) Screening methods and protocols for the identification and purification of the vaccine microorganism: The vaccine microorganism was selected based on its complete dependence on streptomycin. Purity of the vaccine strain was done according to the guidelines set forth in 9 CFR 113.27(d) and reported in the Master Seed report submitted Aug. 31, 2005.

Identification of the vaccine strain was confirmed based on biochemical reactions, dependency on streptomycin sulphate, *Haemophilus parasuis* detection PCR, *H. parasuis* Genotyping PCR, gram staining, and colony morphology. Summary for all testing was reported in the Master Seed Report submitted to USDA-CVB Mar. 23, 2006.

Both the parent and vaccine have been shown to be viable by the American Type Culture Collection (ATCC) and the following ATCC accession numbers have been assigned:

| | |
|---|---|
| *Haemophilus parasuis*: Parent JMSO 50703 | PTA-7710 |
| *Haemophilus parasuis*: JMSO 10134 | PTA-7711 |

Example 3

Vaccine Production

The vaccine culture was started from a working seed. The working seed was subcultured to X+5 by using PPLO media supplemented with 400 mcg/mL streptomycin, 2% dextrose, 10% horse serum, and 0.2% NAD was used. The final subculture was incubated at approximately 37° C. overnight on a shaker cart. Following incubation, the culture was centrifuged for 20 minutes at 3,000 rpms. The cell pellet was resuspended in fresh PPLO media with 1⁄10 of the original volume. The vaccine was stored on ice until used. Immediately prior to vaccination, Trigen was added to the vaccine at 10% of the resuspended volume. Prior to vaccination, the vaccine was titrated and cell concentrations were determined. Cell concentration for the first vaccination was $10^{9.60}$ cells per mL. The vaccine used for animals receiving 2 doses was prepared in the same manner. Cell concentration for the $2^{nd}$ vaccination was $10^{9.55}$ cells per mL.

Example 4

Efficacy of the Vaccine (a) Methods

At arrival, all pigs were injected with 0.3 mL of Excede IM and housed in the same room at the Wilmont Research Farm (WRF) for 7 days. To assure equal representation in treatment groups, pigs were randomly allotted based on litters. Prior to vaccination, non-vaccinated pigs, pigs receiving the vaccine orally, and pigs receiving the vaccine IM were housed in three separate rooms. Pigs receiving a single dose were separated from pigs receiving a $2^{nd}$ dose by a solid partition. Pigs were vaccinated at approximately 4 weeks of age; pigs receiving a second dose were boostered 2 weeks following the first vaccination. Three weeks after the $2^{nd}$ vaccination, all pigs were challenged.

To challenge the pigs, a single ampoule of the *H. parasuis* parent strain, Newport Labs reference 3-0930-1, was pulled from cold storage and streaked on 5 chocolate agar plates. Plates were incubated at 37° C. in candle jars for approximately 48 hours. Using a sterile cotton swab, growth was harvested and used to inoculate 400 mL of PPLO media containing the following supplements: 10% horse serum, 2% dextrose (50%), and 0.2% NAD per mL of PPLO. Cultures were incubated at 37° C. on a shaker cart for approximately 6 hours. Following incubation, % transmittance was recorded, and cell titrations were made. All pigs were challenged intravenously and intraperitoneally with 1 mL per route.

All vaccinations were given at a rate of 0.2 mL per pig IM or orally as appropriate.

(b) Results

Rectal temperatures were taken prior to challenge and for 4 days following challenge. A temperature at or above 40.5° C. was considered a fever. Pigs were weighed prior to challenge, at the time of death or at the end of the study, as appropriate. Average Daily Gain (ADG) was determined for each pig and daily observations were made once daily by a blind observer.

Pigs were observed daily for clinical signs and were scored accordingly. A daily observation chart was constructed using the following scoring system.

| Score | Clinical Signs |
|---|---|
| 4* | Moribund or dead, unable to rise, lateral recumbancy, CNS signs. |
| 3 | Severely lame and or lethargic. Total or complete lameness on one or more limbs, cannot support weight. Extreme difficulty in rising, can stand when prompted, quick to lie down. |
| 2 | Moderately lame and/or lethargic. Lame but will support weight on lame leg, must be prompted to move |
| 1 | Mildly lethargic. Ears are down, not active, slow to rise and move. |
| 0 | Normal |

*Dead pigs are given 4 points for each experimental day following death.

A treatment was considered satisfactory, if, in a valid assay, 80% or more of the vaccinated pigs in the group survived challenge and showed no lesions upon necropsy and at least 80% of the non-vaccinated control pigs do not survive challenge and/or are positive for 1 or more lesions at necropsy. To confirm infection from *H. parasuis* following challenge, lung and heart samples, and peritoneal, joint, and pleural swabs from each necropsied pig were collected and sent to Newport Laboratories (NPL) diagnostic lab for Hps isolation.

The test was valid as 100% of non-vaccinated pigs had lesions or did not survive challenge.

Experiment #1 Homologous protection (serovar 5 inoculation, serovar 5 challenge).

Table 1 shows the mortality rate after inoculation with the vaccine and subsequent challenge with the parent strain.

| Treatment Group | Mortality |
|---|---|
| Non-vaccinates | 100% |
| 1 dose IM vaccinates | 10% |
| 2 dose IM vaccinates | 0% |
| 1 dose oral vaccinates | 80% |
| 2 dose oral vaccinates | 100% |

Table 2 shows the percentage of pigs in each treatment group with a fever.

| Treatment Group | % of animals with a fever |
|---|---|
| Non-vaccinates | 90% |
| 1 dose IM vaccinates | 10% |
| 2 dose IM vaccinates | 0% |
| 1 dose oral vaccinates | 50% |
| 2 dose oral vaccinates | 70% |
| Non-vaccinated/non-challenged | 0% |

Table 3 shows the Average Daily Gain for each treatment group following challenge:

| Treatment Group | Average daily gain (loss) |
|---|---|
| Non-vaccinates | −2.88 lbs/day |
| 1 dose IM vaccinates | 1.65 lbs/day |
| 2 dose IM vaccinates | 1.71 lbs/day |
| 1 dose oral vaccinates | −2.85 lbs/day |
| 2 does oral vaccinates | −5.51 lbs/day |
| Non-vaccinated/non-challenged | 2.21 lbs/day |

Table 4 shows the total points (scores) registered from daily observations.

| Treatment Group | Total Points |
|---|---|
| Non-vaccinates | 116 |
| 1 dose IM vaccinates | 15 |
| 2 dose IM vaccinates | 13 |
| 1 dose oral vaccinates | 112 |
| 2 dose oral vaccinates | 137 |
| Non-vaccinated/non-challenged | 0 |

Experiment 2) Heterologous protection (serovar 5 inoculation, heterologous challenge)

Table 5 shows the mortality % for each treatment group when challenged with a serovar 4 strain.

| Treatment group | Mortality |
|---|---|
| Non-vaccinates | 78% |
| 1 dose vaccinates | 0% |
| 2 dose vaccinates | 0% |

89% of non-vaccinated pigs were positive for one or more lesions commonly associated with *H. parasuis* infection. No vaccinated pigs were necropsied as no vaccinated pig met euthanasia criteria.

Table 6 shows the mortality % for each treatment group when challenged with a serovar 13 strain.

| Treatment group | Mortality |
|---|---|
| Non-vaccinates | 100% |
| 1 dose vaccinates | 13% |
| 2 dose vaccinates | 0% |

All non-vaccinated pigs were positive for 1 or more lesions. Two of 8 pigs vaccinated with a single dose were positive for one or more lesions. One of 8 pigs vaccinated with 2 doses was positive for 1 or more lesions.

All non-vaccinated pigs had fevers following challenge with the parent strain, while all vaccinated pigs had normal temperatures following challenge.

Table 7 shows the Average Daily Gain for each treatment group when challenged by the serovar 5 parent strain, 3-09302-1.

| Treatment Group | Average Daily Gain (loss) |
|---|---|
| Non-vaccinates | −3.84 lbs/day |
| 1 dose vaccinates | 1.65 lbs/day |
| 2 dose vaccinates | 1.71 lbs/day |

Table 8 shows the total points (scores) for each treatment group when challenged by the serovar 5 parent strain, 3-09302-1.

| Treatment Group | Total Points |
|---|---|
| Non-vaccinates | 139 |
| 1 dose vaccinates | 0 |
| 2 dose vaccinates | 0 |

All non-vaccinated pigs had fevers following challenge with the parent strain, while all vaccinated pigs had normal temperatures following challenge.

Challenge with Serotype 4 Strain

All non-vaccinated pigs challenged with strain 4-1230-2 (type 4) had a fever for at least one day. No vaccinated pigs had fevers following challenge.

Table 9 shows the Average daily gain for each treatment group following challenge with the serotype 4, 4-1230-2 strain.

| Treatment Group | Average Daily Gain (loss) |
|---|---|
| Non-vaccinates | −2.43 lbs/day |
| 1 dose vaccinates | 1.27 lbs/day |
| 2 dose vaccinates | 1.86 lbs/day |

Table 10 shows Total points (scores) registered from daily observations were.

| Treatment Groups | Total Points |
|---|---|
| Non-vaccinates | 99 |
| 1 dose vaccinates | 0 |
| 2 dose vaccinates | 0 |

Challenge with Serotype 13 Strain

All non-vaccinated pigs challenged with strain 5-1124-23 (type 13) had a fever for at least one day following challenge. Four pigs from the 1 dose vaccinates had a fever for one or more days following challenge and 1 pig from the 2 dose vaccinates had a fever for one or more days.

Table 11 shows the Average Daily Gain for each treatment group following challenge with the serotype 13, 5-1124-23 strain.

| Treatment Groups | Average Daily Gain (loss) |
|---|---|
| Non-vaccinates | −4.12 lbs/day |
| 1 dose vaccinates | 0.99 lbs/day |
| 2 dose vaccinates | 0.79 lbs/day |

Table 12 shows the Total points (scores) registered from daily observations.

| Treatment Groups | Total Points |
|---|---|
| Non-vaccinates | 120 |
| 1 dose vaccinates | 15 |
| 2 dose vaccinates | 6 |

Discussion/Conclusions: The *H. parasuis* ML (modified live) vaccine had clear protection against all 3 challenge strains. Mortality, ADG, daily observations, and body temperature data all support the efficacy of and the potential for the ML vaccine to be used as a tool for controlling disease caused by *H. parasuis*. Results support the efficacy of the vaccine against heterologous challenge strains.

Example 5

Mutant Characterization Using DNA Sequencing

Materials and Methods:

PCR/Sequencing Primer Development:

The *Haemophilus influenzae* streptomycin resistance (strA) gene was used as a model for primer development as there was little published sequence data for *H. parasuis*. A freeware primer selection software was used to select primers for this gene.

```
stra Forward SEQ ID NO: 5.

stra Reverse SEQ ID NO: 6.
```

Genomic DNA Extraction:

Cultures of the parent and the JMSO strain were swabbed onto multiple agar media (Chocolate agar for parent strain, PPLO agar with 400 mg/mL of streptomycin for the JMSO strain). Plates were incubated at 37° C.+/−3 in a candle jar until sufficient lawn of growth was obtained (approx. 48 hrs).

The Qiagen Genomic DNA extraction kit was used to obtain the DNA for sequencing. The method was as follows:

Aseptically, 5 mL of 0.25% Tryptic Soy Broth (TSB) was added to each plate. With a sterile loop, the growth was scraped off the agar surface, the plate was tipped to the side and the bacterial suspension was collected with a pipet and pooled into a tared centrifuge tube. The suspensions were centrifuged at 4,500 rpm for 10 min. The supernatant was decanted and the remaining pellet was weighed (for calculation of extraction lysis steps). Pelleted cells were frozen until lysis could be conducted.

Buffer B1 was prepared by adding 100 mg/mL solution of RNase A to obtain a final concentration of 200 ug/mL. Eleven mL of Buffer B1 was added to the frozen pellets and the tubes vortexed until a uniform suspension was obtained. To the suspension, 300 ul of a lysozyme stock (100 mg/ml) and 500 ul of Proteinase K were added. The tubes were incubated at 37° C.+/−3 for 1 hr. The sample was deproteinized with Buffer B2, by adding 4 ml to the suspension. The tube was vortexed for a few seconds and then was placed in a water bath at 50° C. for 30 min.

A 500/G Genomic Tip (provided in the kit) was set up for each of the parent and JMSO digested pellets. The tips were equilibrated with 10 ml of Buffer QBT. The tip was emptied by gravity flow. The digested pellet was vortexed for 10 sec at maximum speed and diluted 1:1 with Buffer QBT. One half of the total volume of the digested pellet was poured into the Genomic Tip. A syringe plunger was used to apply positive pressure to help the eluation (20-40 drops/min maximum flow rate). The Genomic Tip was then washed twice with 15 ml of Buffer QC. The genomic DNA was then eluted into a sterile tube with 15 ml of Buffer QF. The DNA was then precipitated with 10.5 ml of room temperature isopropanol by mixing and centrifuging at >5000×g for 15 min. The supernatant was removed and the DNA pellet washed with 4 ml of cold 70% ethanol. The pellets were vortexed and the samples centrifuged briefly. The supernatant was carefully removed and the remaining DNA pellet was allowed to air dry for 5-10 minutes. The DNA pellet was resuspended in TE buffer (pH 8.0) and the DNA allowed to dissolve overnight at 37° C.+/−3.

The resuspended DNA was then evaluated using a 2% agarose gel. The evaluation revealed high molecular weight DNA. The DNA was then quantified using a UV Spectrophotometer for the PCR amplification.

Amplification of Target Gene:

Amplification of the strA gene was conducted on the genomic DNA samples. Approximately 20 ng of DNA was used in this reaction. The "per reaction mix" consisted of the following: 37.8 ul of sterile molecular grade water, 5.0 ul of Taq DNA polymerase buffer (provided with Taq), 1.0 ul of dNTP mix (100 uM each), 10 uM of each forward and reverse primers, and 0.2 ul of Taq DNA polymerase (Eppendorf). The samples were amplified at the following conditions: 94° C. for 5 min., followed by 30 cycles of 94° C. for 30 sec., 54° C. for 20 sec., and 68° C. for 30 sec.

DNA Sequencing:

The PCR product was purified of residual dNTPs and Taq DNA polymerase in preparation for sequencing using the QIAquick PCR Purification Kit (Qiagen). The purified PCR product was resolved on a 2% agarose gel, to estimate quantity for sequencing step.

A Dye Terminator Cycle Sequencing (DTCS) and a Beckman Coulter CEQ 8000 (Beckman Coulter) were used to sequence this product. The reaction was set up per the recommendations in the DTCS Quick Start Master Mix kit provided by Beckman Coulter. Forward and reverse sequence reactions were set up using 0.15 uM of primer.

Results:

The sequencing parameters resulted in the complete strA gene. A BLAST search revealed that the sequence obtained was an exact match to the strA gene of *H. influenzae*. Both forward and reverse sequences were obtained, thru multiple repetitions. The sequences were analyzed using MegAlign (DNA Star) software and a consensus sequence was obtained. The alignment and comparison of the parent and JMSO consensus sequences revealed two nucleotide changes, coding for two amino acid differences. Nucleotide 68: GCA (Alanine) parent to GAA (Glutamic Acid) JMSO strain. Nucleotide 272: CCG (Proline) parent to CTG (Leucine) JMSO.

The nucleotide and sequence data are identified in a sequence listing document filed with this application.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described below. All publications, patent applications, patents, and other references mentioned herein are incorporated by reference in their entirety to the extent allowed by applicable law and regulations. In case of conflict, the present specification, including definitions, will control.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. A culture of cells of an isolated strain derived from a pathogenic parent strain of *Haemophilus parasuis*, wherein said cells exhibit attenuated pathogenicity in pigs as compared to those of the parent strain and wherein said cells are capable of triggering an immune response that protects the pig against *Haemophilus parasuis* infection when administered as a live vaccine, wherein the isolated strain was derived from the pathogenic parent strain by MNNG mutagenesis, and wherein the isolated strain is dependent on streptomycin for growth.

2. The cell culture of claim 1, wherein the parent strain and the isolated strain are serovar 5 of *Haemophilus parasuis.*

3. A vaccine for protecting pigs against infection by *Haemophilus parasuis*, comprising a veterinarily acceptable carrier and an immunologically effective amount of live cells of an isolated strain of a serovar derived from a pathogenic parent strain of *Haemophilus parasuis*, wherein said cells exhibit attenuated pathogenicity in pigs as compared to those of the parent strain and wherein said cells are capable of triggering an immune response that protects the pig against *Haemophilus parasuis* infection when administered as a live vaccine, wherein the parent strain and the isolated strain are serovar 5 of *Haemophilus parasuis*, wherein the vaccine provides heterologous protection against at least serovars 4 and 13.

4. The vaccine of claim 3, wherein the isolated strain was derived from the pathogenic parent strain by chemical mutagenesis.

5. The vaccine of claim 4, wherein the isolated strain is dependent on streptomycin for growth, the parent strain and the isolated strain each having a streptomycin resistance (strA) gene.

6. The vaccine of claim 5, wherein the DNA sequence of the strA gene of the parent strain is SEQ ID NO: 1 and wherein the DNA sequence of the strA gene of the isolated strain is SEQ ID NO: 2.

7. The vaccine of claim 6, wherein the protein encoded by the strA gene of the parent strain is SEQ ID NO: 3 and wherein the protein encoded by the strA gene of the isolated strain is SEQ ID NO: 4.

8. The vaccine of claim 5, wherein the strA gene of the isolated strain differs from the strA gene of the parent strain and wherein the difference comprises a change at nucleotide 68 from C to A and a change at nucleotide 272 from C to T.

9. The vaccine of claim 8, wherein the protein encoded by the strA gene of the isolated strain differs from the protein encoded by the strA gene of the parent strain and wherein the difference comprises a change at residue 23 from alanine to glutamic acid and a change at residue 91 from proline to leucine.

10. A method of preparing a culture of attenuated cells derived from a pathogenic parent strain of *Haemophilus parasuis*, comprising modifying cells from said pathogenic parent strain, selecting and clonally propagating one or more modified cells that exhibit attenuated pathogenicity in pigs compared to cells of the parent strain, and selecting and clonally propagating one or more attenuated cells which are capable of triggering an immune response that protects the pig against *Haemophilus parasuis* infection when administered as a live vaccine.

11. The method of claim 6, wherein the culture of attenuated cells was modified from the pathogenic parent strain by chemical mutagenesis.

12. The method of claim 7, wherein the culture of attenuated cells is dependent on streptomycin for growth.

13. The method of claim 7, wherein the parent strain and the culture of attenuated cells are serovar 5 of *Haemophilus parasuis*.

14. A method for preparing a vaccine to protect pigs against *Haemophilus parasuis* infection, comprising modifying cells from a serovar of a pathogenic parent strain, selecting and clonally propagating one or more modified cells that exhibit attenuated pathogenicity in pigs compared to cells of the parent strain, and selecting and clonally propagating one or more attenuated cells which are capable of triggering an immune response that protects the pig against *Haemophilus parasuis* infection when administered as a live vaccine, and combining an immunologically effective amount of the attenuated cells with a veterinarily acceptable carrier in a form suitable for administration as a live vaccine to the pig.

15. The method of claim 10, wherein the attenuated cells were modified from the pathogenic parent strain by chemical mutagenesis.

16. The method of claim 10, wherein the attenuated cells are dependent on streptomycin for growth.

17. The method of claim 10, wherein the parent strain and the attenuated cells are serovar 5 of *Haemophilus parasuis*.

18. The method of claim 13, wherein the vaccine provides heterologous protection against other serovars.

19. The method of claim 14, wherein the vaccine provides protection against at least serovars 4 and 13.

20. A vaccine for protecting pigs against infection by *Haemophilus parasuis*, comprising a veterinarily acceptable carrier and an immunologically effective amount of live cells of an isolated strain of a serovar derived from a pathogenic parent strain of *Haemophilus parasuis*, wherein said cells exhibit attenuated pathogenicity in pigs as compared to those of the parent strain and wherein said cells are capable of triggering an immune response that protects the pig against *Haemophilus parasuis* infection when administered as a live vaccine, wherein the isolated strain was derived from the pathogenic parent strain by chemical mutagenesis, wherein the isolated strain is dependent on streptomycin for growth, the parent strain and the isolated strain each having a streptomycin resistance (strA) gene.

21. The vaccine of claim 20, wherein the parent strain and the isolated strain are serovar 5 of *Haemophilus parasuis*.

22. The vaccine of claim 21, wherein the vaccine provides heterologous protection against other serovars.

23. The vaccine of claim 22, wherein the vaccine provides heterologous protection against at least serovars 4 and 13.

24. The vaccine of claim 20, wherein the DNA sequence of the strA gene of the parent strain is SEQ ID NO: 1 and wherein the DNA sequence of the strA gene of the isolated strain is SEQ ID NO: 2.

25. The vaccine of claim 20, wherein the protein encoded by the strA gene of the parent strain is SEQ ID NO: 3 and wherein the protein encoded by the strA gene of the isolated strain is SEQ ID NO: 4.

26. The vaccine of claim 24, wherein the strA gene of the isolated strain differs from the strA gene of the parent strain and wherein the difference comprises a change at nucleotide 68 from C to A and a change at nucleotide 272 from C to T.

27. The vaccine of claim 25, wherein the protein encoded by the strA gene of the isolated strain differs from the protein encoded by the strA gene of the parent strain and wherein the difference comprises a change at residue 23 from alanine to glutamic acid and a change at residue 91 from proline to leucine.

* * * * *